(12) United States Patent
Purcell et al.

(10) Patent No.: US 10,046,053 B2
(45) Date of Patent: *Aug. 14, 2018

(54) PROTEASE TRIGGERED RELEASE OF MOLECULES FROM HYDROGELS

(71) Applicant: The Trustees of the University of Pennsylvania, Philadelphia, PA (US)

(72) Inventors: Brendan Patrick Purcell, Brooklyn, NY (US); Jason Alan Burdick, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/628,766

(22) Filed: Jun. 21, 2017

(65) Prior Publication Data
US 2018/0028672 A1   Feb. 1, 2018

Related U.S. Application Data

(60) Continuation-in-part of application No. 15/601,085, filed on May 22, 2017, now Pat. No. 9,919,054, which is a division of application No. 13/805,501, filed as application No. PCT/US2011/040811 on Jun. 17, 2011, now Pat. No. 9,694,081.

(60) Provisional application No. 61/356,800, filed on Jun. 21, 2010.

(51) Int. Cl.
| | | |
|---|---|---|
| *A61K 38/00* | (2006.01) |
| *A61K 47/42* | (2017.01) |
| *A61K 38/10* | (2006.01) |
| *A61K 38/18* | (2006.01) |
| *A61K 9/06* | (2006.01) |
| *A61K 47/24* | (2006.01) |
| *A61K 38/57* | (2006.01) |

(52) U.S. Cl.
CPC ............... *A61K 47/42* (2013.01); *A61K 9/06* (2013.01); *A61K 38/10* (2013.01); *A61K 38/1866* (2013.01); *A61K 38/57* (2013.01); *A61K 47/24* (2013.01)

(58) Field of Classification Search
None
See application file for complete search history.

(56) References Cited

U.S. PATENT DOCUMENTS

2009/0269405 A1   10/2009   Windsor et al.

*Primary Examiner* — Jeannette M Lieb
(74) *Attorney, Agent, or Firm* — Baker & Hostetler LLP

(57) ABSTRACT

The invention relates to compositions comprising (i) biocompatible hydrogel and (ii) one or more therapeutic agents contained within said hydrogel; wherein the hydrogel is cross-linked utilizing a cross-linker comprising a peptide sequence that is capable of being degraded by an enzyme; the therapeutic agent being effective as a treatment of a condition related to the presence of the enzyme.

27 Claims, 9 Drawing Sheets

Synthesis 1: HA-Aldehyde Synthesis

Synthesis 2: HA-Hydrazide Synthesis

Gel formation through mixing of Synthesis 1 and Synthesis 2:
Hydrazone formation via Hydrazide-Aldehyde reaction Gelation time 8-9 min Gelation time 2-3 min Gelation/properties controlled by HA modification and ratio of HA-Aldehyde to HA-Hydrazide

MMP-specific gel

Peptide crosslinker that responds to MMP-1, MMP-2

```
                        SEQUENCE LISTING

<160> NUMBER OF SEQ ID NOS: 9

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gln Gly Ile Trp Gly Gln
1               5

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gln Gly Ile Ala Gly Gln
1               5

<210> SEQ ID NO 3
<211> LENGTH: 8
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Pro Gln Gly Ile Trp Gly Gln
1               5

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Pro Gln Gly Ile Ala Gly Gln
1               5

<210> SEQ ID NO 5
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Cys Arg Asp Gly Pro Gln Gly Ile Trp Gly Gln Asp Arg Cys Gly
1               5                   10                  15

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Gly Pro Gln Gly Ile Trp Gly Gln Gly Cys Gly
1               5                   10

<210> SEQ ID NO 7
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Cys Gly Gln Gly Trp Ile Gly Gln Pro Gly Gly Gly
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Asp Gly Pro Gln Gly Ile Trp Gly Gln Asp Gly
```

-continued

```
<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Cys Gly Tyr Gly Arg Gly Asp Ser Pro Gly
1               5                   10
```

PROTEASE TRIGGERED RELEASE OF MOLECULES FROM HYDROGELS

CROSS REFERENCE TO ELATED APPLICATIONS

The present application is a continuation in part of U.S. patent application Ser. No. 15/601,085, filed May 22, 2017, which is a divisional of U.S. patent application Ser. No. 13/805,501, filed Mar. 6, 2013, which is the U.S. national phase application of PCT/US2011/040811, filed Jun. 17, 2011, which claims benefit of U.S. Provisional Patent Application No. 61/356,800, filed Jun. 21, 2010, the disclosures of each are incorporated herein in their entireties.

GOVERNMENT RIGHTS

This invention was made with government support under Contract No. R01 HL111090 awarded by the National Institutes of Health (NIH). The government has certain rights in the invention.

SEQUENCE LISTING

The instant application contains a Sequence Listing which has been submitted electronically in ASCII format and is hereby incorporated by reference in its entirety. Said ASCII copy, created on Oct. 9, 2017, is named 103241_000986_SL.txt and is 2,547 bytes in size.

TECHNICAL FIELD

The present invention concerns the use of hydrogels to locally deliver pharmaceuticals/factors based on elevated local enzyme levels.

BACKGROUND

Matrix metalloprotease (MMPs) are calcium dependent, zinc containing enzymes that degrade a wide range of extracellular proteins as well as process bioactive molecules into an active form. In humans, there are over two dozen known MMPs and these are conserved through many vertebrate animals and have also been found in invertebrates and plants. These include MMP-1, 2, 3, 7, 8, 9, 10, 11, 12, 13, 14, 15, 16, 17, 18, 19, 20, 21, 22, 23A, 23B, 24, 25, 26, 27, and 28. Under normal physiological conditions, MMP activity is precisely controlled—such as through tissue inhibitors of MMPs (TIMPs)—to maintain a low level of structural protein, cell receptor, and growth factor turnover. However, under pathophysiological conditions, there is a persistence of MMP activity that causes maladaptive changes to tissue architectures and functions, contributing to disease progression.

Excessive extracellular matrix (ECM) proteolysis by MMPs is a hallmark of many human disease states including chronic inflammation, tumour progression and cardiovascular disease. The induction of MMPs has been shown to play a role in abdominal, thoracic and aortic aneurysms, multiple forms of cancer, rheumatoid arthritis, osteoarthritis, restenosis, myocardial infarction, stroke, rosacea, eye disease, chronic obstructive pulmonary disease, psoriasis, macular degeneration, multiple sclerosis, myocardial rupture, left ventricular hypertrophy, and Kaposi's sarcoma.

In order to treat these indications, the design and development of molecules that inhibit MMP activity has been a widely explored area of research over the past 25 years. These molecules include those based on hydroxymates and non-hydroxymate chemistries including thiol, phosphinyl, tetracycline, mercaptoalkylpeptidyl, 6,7-dihydroxy-coumarin, carboxylate, and bis-sulfonamide. Further novel inhibitors including peptide sequences, and molecules derived from shark cartilage extract have been developed. Unfortunately none of these MMP inhibitors have been translated to clinical application owing to the dose-limiting side effects following systemic administration of these molecules. While many of these molecules are potent inhibitors of MMPs, they do so through non-specific interactions such as catalytic zinc ion chelation or binding to the side pocket of the enzyme. Further, all MMPs share significant sequence and structural homology. As a result, these inhibitors have poor selectivity for specific MMP enzymes which may be implicated in a targeted disease, and therefore have off-target effects when delivered systemically due to broad spectrum MMP inhibition throughout the body. For example, muscloskeletal syndrome or pain and stiffness in the joints was commonly reported during clinical trials where MMP inhibitors were delivered systemically to treat myocardial infarction in patients.

To limit off-target effects of therapeutics, biomaterials—including injectable and water-swollen polymer networks or hydrogels—have acted as depots to locally deliver therapeutics through diffusion and degradation mechanisms. Typically, these material systems are engineered to achieve a release profile to adequately dose patients within a therapeutic window specific to a disease. However, the absolute magnitude and temporal variation of MMP activity in patients is highly variable; therefore, one hydrogel formulation and inhibitor dose may not be widely applicable across patient populations.

The present invention described in this patent application address these concerns of broad spectrum MMP inhibitors by encapsulating them in an injectable hydrogel technology that targets delivery of the inhibitors to a diseased tissue and releases the inhibitors in response to elevated MMP activity. Importantly, the inhibitors are sequestered in the hydrogel through non-covalent interactions including hydrophobic, electrostatic, Van der Walls, and polarization forces. MMP specificity can be designed into the hydrogel by engineering the sequence of the MMP degradable crosslinker. Further, the physical properties of the hydrogel can be controlled to ensure localization in a wide range of diseased tissues where elevated MMP activity contributes to disease progression.

Cardiac problems are a major global health concern. According to the American Heart Association, 1.26 million people suffer from heart attacks annually. If the patient survives, they are at a high risk for developing heart failure. Left ventricular remodeling contributes to heart failure, which in 1995, affected 2 million people (Schocken et al, J Am Coll Cardiol. 1992 August; 20 (2):301-6). The incidence and death by heart failure has been steadily increasing for years, suggesting that the potential patient population may continue to grow significantly over time. Many therapeutic approaches, both pharmacologic and surgical, have been developed to treat heart failure. Most therapies are directed at patients who have already developed symptoms. Few if any are directed at patients in the early post myocardial infarction time period before symptoms develop. None are directed at limiting extracellular matrix destruction by matrix metalloprotease. Typically, a patient suffering a heart attack is given a cocktail of medicines that can be difficult to titrate and manage. Efficacy is often not achieved. The population of heart failure patients continues to grow in spite of the current therapeutic armamentarium.

In a paper published in Circulation (June 2003, p 2857), Wilson et al determined that certain matrix metalloprotease (MMP), such as MMP-13 are upregulated post-MI, perhaps resulting in the left ventricular remodeling that adversely affects heart function. Further, they found that the antagonist to MMP-13, TIMP, is down-regulated. In particular, this study demonstrated increased levels of MMP-13 and MT1-MMP after MI, which may have particular significance with respect to pathological remodeling. Specifically, MMP-13 is increased in end-stage cardiomyopathies and aggressive breast carcinomas. MMP-13 degrades fibrillar collagens and therefore may contribute to myocardial extracellular remodeling. Increased MT1-MMP levels within the transition and MI regions may have particular significance, for two reasons. First, MT1-MMP degrades a wide range of extracellular matrix proteins. Second, MT1-MMP can proteolytically process soluble pro-MMPs, such as pro-MMP-13,2 and thereby amplify local proteolytic activity. The LV regions in which this local induction of MT1-MMP and MMP-13 occurred were paralleled by decreased TIMP levels. The present study demonstrated that increased MT1-MMP levels and decreased TIMP-4 levels were correlated to the extent of regional LV remodeling. This regional imbalance between these specific MMPs and TIMPs probably contributed to continued regional expansion in the post-MI myocardium.

There is a need in the art for treatments to minimize left ventricular remodeling associated with MI. In addition to LV remodeling uses, there is also a need in the art to provide regional delivery of MMP inhibiting therapy that would be active only where MMP's are active.

SUMMARY

In some aspects, the invention concerns compositions comprising a biocompatible hydrogel; and a therapeutic agent contained within the hydrogel. The hydrogel is cross-linked utilizing a cross-linker comprising a peptide sequence that is capable of being degraded by an enzyme; said therapeutic agent being effective as a treatment of a condition related to the presence of said enzyme. In some embodiments, the therapeutic agent is a inhibitor of matrix metalloproteinase. In certain embodiments, such therapeutics include tissue inhibitor of matrix metalloproteinase contained within the hydrogel and the hydrogel is cross-linked utilizing a cross-linker comprising a peptide sequence that is capable of being degraded by a matrix metalloproteinase; the matrix protease being inhibited by said inhibitor of matrix metalloproteinase. In certain embodiments, the inhibitor of matrix metalloproteinase is a hydroxymate based compound such as ilomastat. In some embodiments, the inhibitor of matrix metalloproteinase is a tetracycline based compound such as doxycycline or a modified doxycycline.

In some compositions, the hydrogel comprises one or more of hyaluronic acid, sulfated hyaluronic acid, sulfonated hyaluronic acid, dextran, dextran sulfate, sulfonated dextran, chondroitin sulfate, heparin and heparan sulfate.

Certain compositions have the peptide sequence incorporated into the cross-linker via reaction of thiol groups of cysteines with acrylates or methacrylates. Some compositions have a cross-linker that comprises the peptide sequence and at least one of hyaluronic acid or polyethylene glycol. Some compositions consist of reaction of an aldehyde-containing molecule with a hydrazide group on the end of the peptide.

In some embodiments, the inhibitor of matrix metalloproteinase is TIMP-3, doxycycline or ilomastat. In certain embodiments, the matrix metalloproteinase is MMP-1, MMP-2, MMP-8, MMP-9 or MMP-13.

Another aspect of the invention concerns methods for treating myocardial infarction comprising administering to a patient in need of such treatment a composition disclosed herein. In some embodiments, the patient is a mammal. In some preferred embodiments, the patient is a human.

Yet another aspect of the invention concerns compositions and methods described herein for treatment of osteoarthritis, meniscal repair, ligament repair, and aortic aneurisms.

Another aspect of the invention concerns methods for treating osteoarthritis comprising administering to a patient in need of such treatment a composition disclosed herein. In some embodiments, the patient is a mammal. In some preferred embodiments, the patient is a human. Other methods comprise treatment of osteoarthritis, aortic aneurisms, meniscal repair or ligament repair.

Yet another aspect of the invention concerns methods of delivery of an inhibitor of matrix metalloproteinase comprising: (i) administering a hydrogel of disclosed herein to a patient; (ii) allowing the hydrogel to contact matrix metalloproteinase; and (iii) the contact resulting in the release of at least a portion of said inhibitor of matrix metalloproteinase. In some embodiments, the delivery is accomplished through a syringe or catheter.

BRIEF DESCRIPTION OF THE DRAWINGS

FIG. 3 discloses SEQ ID NO: 8.

FIG. 4 discloses SEQ ID NO: 6.

FIG. 7 discloses SEQ ID NO: 7.

FIG. 9 discloses SEQ ID NOS 9 and 5, respectively, in order of appearance.

DETAILED DESCRIPTION OF ILLUSTRATIVE EMBODIMENTS

Figure 1:
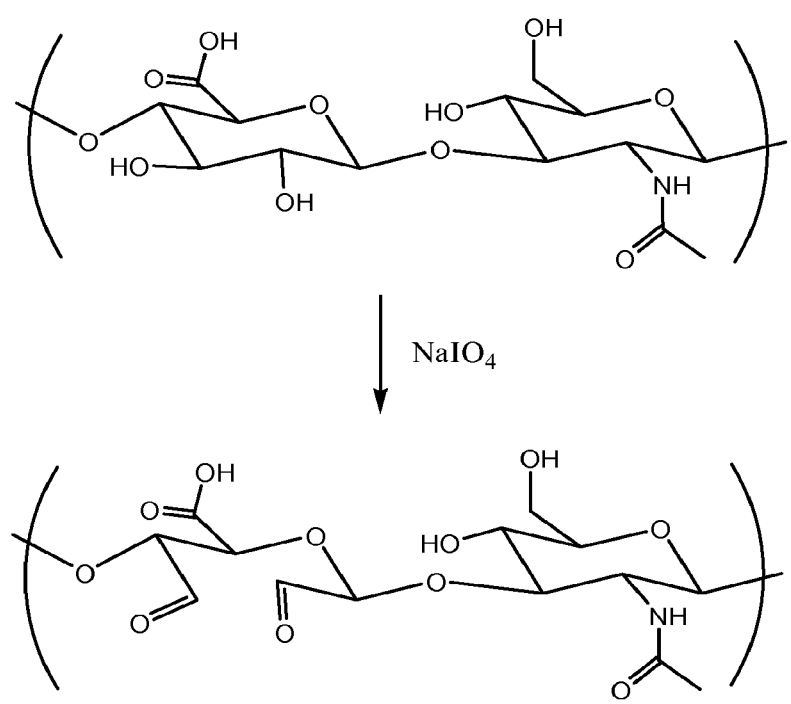
FIG. 1 illustrates synthesis of HA-aldehyde (Synthesis 1) for use in forming a hydrogel.

The present invention may be understood more readily by reference to the following detailed description taken in connection with the accompanying figures and examples, which form a part of this disclosure. It is to be understood that this invention is not limited to the specific devices, methods, applications, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

It is to be appreciated that certain features of the invention which are, for clarity, described herein in the context of separate embodiments, may also be provided in combination in a single embodiment. Conversely, various features of the invention that are, for brevity, described in the context of a single embodiment, may also be provided separately or in any subcombination. Further, reference to values stated in ranges include each and every value within that range.

Hydrogels containing degradable cross-linkers can be utilized in the delivery of therapeutic and/or diagnostic agents to a specified site within a patient. In the present invention, the cross-linkers comprise a peptide sequence that is degradable by particular enzymes. When one utilizes a hydrogel containing a therapeutic agent to a condition that is associated with the presence of a particular enzyme, one can selectively deliver the agent to a specified target within the patient because the enzyme will cause degradation of the cross-links which will result in release of the agent.

Any peptide sequence containing linking group that is capable of being degraded by the desired enzyme can be utilized. In some embodiments, the peptide is at least two units in length. While the peptide has no maximum length so long as it is degradable by the desired enzyme, in certain embodiments, the peptide is up to 20, 30, 50 or 100 units in length. Some peptides are at least 5 or 10 units in length. Each of these upper and lower limits are intended to be combinable to reflect some preferred peptide lengths. Examples of suitable peptides include those containing the QGIWGQ (Seq. ID No. 1) or QGIAGQ (Seq. ID No. 2) sequence from collagen including GPQGIWGQ (Seq. ID No. 3), GPQGIAGQ (Seq. ID No. 4), GCRDGPQGI-WGQDRCG (Seq. ID No. 5), GGPQGIWGQGCG (Seq. ID No. 6), GCGQGWIGQPGGG (Seq. ID No. 7) and collagen or gelatin itself.

One application concerns treatment of myocardial infarction (MI). Left ventricular (LV) remodeling after myocardial infarction, for example, is a common structural event and contributes to increased morbidity and mortality. Matrix metalloprotease (MMPs) have been demonstrated to contribute to LV remodeling after MI by contributing to the breakdown of interstinal matrix proteins like collagen and elastin. We have demonstrated that upregulation of MMPs and down regulation of their naturally occurring inhibitors, tissue inhibitors of matrix metalloprotease (TIMPs), occur in a type, region and temporal specific manner within the myocardium after MI. The use of a broad spectrum, systemically delivered MMP inhibitor is associated with significant adverse reactions. The ability to inhibit specific MMPs in specific regions of the heart at specific times after MI will lead to improved outcomes after MI for a large number of patients.

Regional delivery of MMP inhibiting therapy that would be active only where MMP's are active can also be utilized in treatments of other conditions. Arthritis is an example of another disease where this approach could be useful. Any disease state where localized release of therapeutics where certain MMPs exist may be treated by the hydrogel systems of the invention.

One concept that is disclosed herein is the use of synthetic hydrogels that incorporate peptide sequences that degrade in the presence of certain enzyme/proteases. The degradation or breaking of these crosslinks in the hydrogel alters the crosslinking density, which in turn alters the material properties (i.e. mechanics), which alters the diffusion of molecules through the hydrogel and hence delivery into the affected tissue. One area where this approach would be important is in disease processes where there are region specific changes in the levels of MMPs. An important example of such a pathologic phenomenon is post-MI LV remodeling. There may be target molecules (e.g., MMP inhibitors) that can alter MMP activity and treat or prevent this disease. With a material such as this, the release of these molecules will be locally dependent on the level of protease activity at those sites. For example MMP-13 is known to be up-regulated in the pen-infarct region in the first 8 weeks after MI and TIMP-3 (an inhibitor of MMP-13) down regulated during this time period; a hydrogel that is degraded only in the presence of MMP-13 and released TIMP-3 locally as it was degraded would likely have a beneficial effect on LV remodeling.

Hydrogels are well known in the art and are generally formed by the reaction of a macromer having a biocompatible backbone with a cross-linking agent. Any suitable hydrogel may be utilized. Types of materials that could be used for this purpose include crosslinked synthetic hydrogels that are based on molecules like hyaluronic acid or polyethylene glycols. Suitable hydrogels also include those constructed using polyesters, polyurethanes, polysaccharides, proteins, and combinations thereof. Polyesters, poly(ethylene oxide) (PEO), proteins such as collagen or gelatin and the like are also suitable polymeric materials can also be used as a polymeric component of the hydrogel. General synthetic methods for making hydrogels can be found, for example in Burdick, et al, Soft Matter, 2009, 5, 1601-1606.

Some hydrogels comprises one or more of hyaluronic acid, sulfated hyaluronic acid, sulfonated hyaluronic acid, dextran, dextran sulfate, sulfonated dextran, chondroitin sulfate, heparin and heparan sulfate.

A partial listing of polysaccharides that are useful in the claimed invention includes hyaluronic acid, amylase, amylopectin, glycogen, cellulose, heparin, agarose, alginate, and the like. In some embodiments, hyaluronic acid or any combination thereof is particularly suitable for use in the instant invention. In some embodiments—such as those embodiments that include hyaluronic acid—the biocompatible backbone unit is capable of enzymatic degradation.

In other embodiments, the biocompatible backbone is capable of hydrolytic degradation. Those embodiments are considered useful where a user may desire a degradable macromer whose degradation is dependent primarily on exposure to aqueous medium without the additional complication of a macromer that is also susceptible to enzymatic degradation. In some embodiments, the macromer is capable of both enzymatic and hydrolytic degradation.

The macromers may include a range of polymerizing moietes, such as acrylates, methacrylates, and the like. In some embodiments, the polymerizing moiety includes a carbon-carbon double or triple bond. The moiety is suitably polymerized by photopolymerization, by free radical-initiation, or by other methods of polymerization known to those of skill in the art.

The peptide moieties can be incorporated into the cross-linkers by reaction of active hydrogen atoms. In some embodiments, the active hydrogen atoms can be part of hydroxy, thiol, or amine groups (including hydrazine). In some embodiments, the peptide can be incorporated as crosslinks through the addition reaction of thiols in cysteines in the peptides with acrylate or methacrylates, vinyl sulfones, or maleimides on these molecules.

Any inhibitor of MMPs can be utilized with the present invention. In some embodiments, hydroxymate based inhibitors (ilomastat, batimastat, or marimastat for example) or non-hydroxymate based inhibitor (doxycycline or modified doxyclines for example).

In some embodiments, the therapeutic molecule may be directly encapsulated during the gelation process by mixing the molecule with the pre-cursor solutions.

The compositions of the instant invention may be administered by methods well known to those skilled in the art. Such methods include local or systemic administration. In some embodiments, administration is topical. Such methods include ophthalmic administration and delivery to mucous membranes (including vaginal and rectal delivery), pulmonary (including inhalation of powders or aerosols; intratracheal, intranasal, epidermal and transdermal), oral or parenteral. Parenteral administration includes intravenous, intraarterial, subcutaneous, intraperitoneal or intramuscular injection or infusion; or intracranial (including intrathecal or intraventricular, administration); or into the joint (including knee, hip or shoulder); or into the spine.

Pharmaceutical compositions and formulations for topical administration include but are not limited to ointments, lotions, creams, transdermal patches, gels, drops, suppositories, sprays, liquids and powders. Utilization of conventional pharmaceutical carriers, oily bases, aqueous, powder, thickeners and the like may be used in the formulations.

The pharmaceutical compositions may also be administered in tablets, capsules, gel capsules, and the like.

Penetration enhancers may also be used in the instant pharmaceutical compositions. Such enhancers include surfactants, fatty acids, bile salts, chelating agents, and non-chelating non-surfactants. Such enhancers are generally described in U.S. Pat. No. 6,287,860, which is incorporated herein by reference.

In addition to treatment of diseases or other conditions, compositions disclosed herein may also be useful prophylactically.

In some preferred embodiments, the hydrogels can be delivered locally either via implantation or as an injection procedure, potentially through syringes or catheters.

Due to the variety of therapeutic agents that can be utilized with the cross-linked hydrogel systems, a wide variety of diseases and disorders can be treated with the technology described herein. Post MI remodeling is one application of the proposed therapeutic approach. In addition, the disclosed concept could be applied in any ailment in which MMPs contribute to the pathophysiology of the disease. Treatment methods comprise administration of the instant compositions by any appropriate method to a patient in need of such treatment. In some embodiments, the patent is a mammal. In certain preferred embodiments, the patient is a human.

The invention is illustrated by the following examples which are intended to be illustrative and not limiting in scope.

EXAMPLES

Unless noted otherwise, all percentages are by weight.

Example 1: Synthesis of HA-Aldehyde

Figure 2:
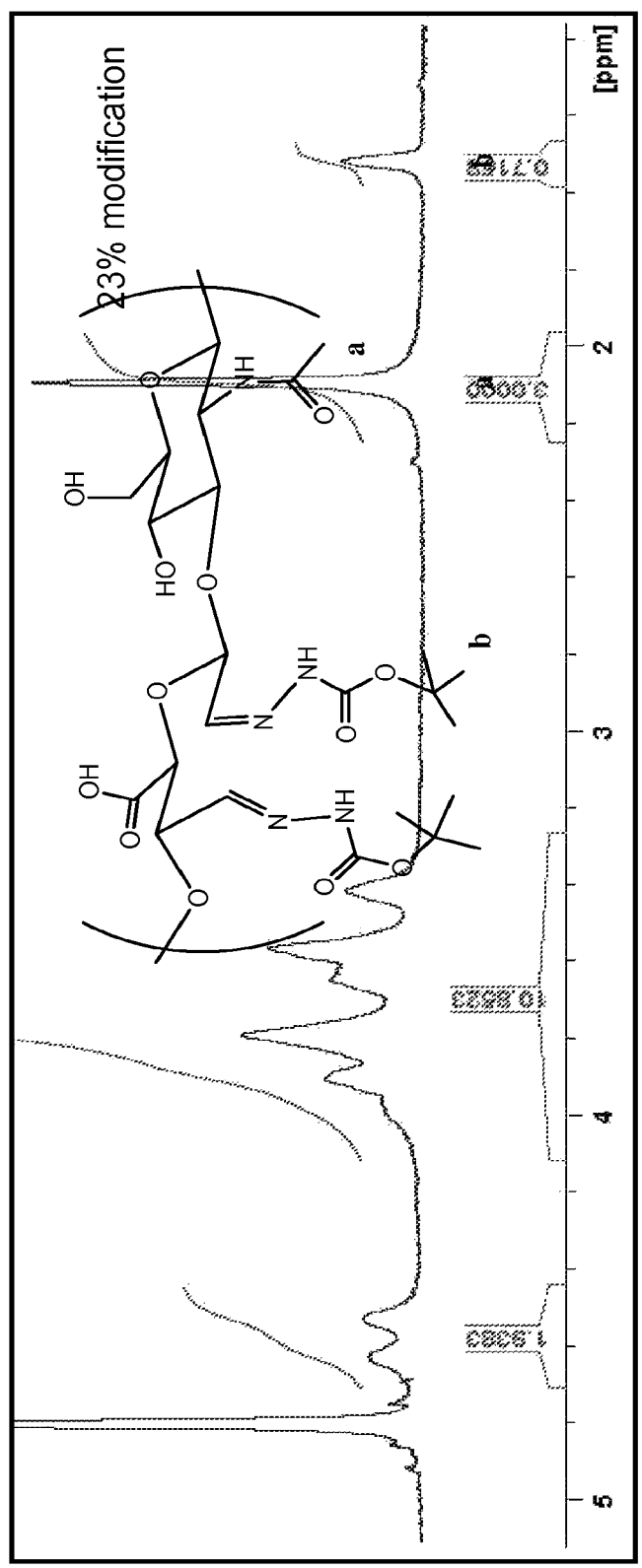
FIG. 2 presents analytical analysis of the HA-aldehyde shown in FIG. 1.

Hyaluronic acid (HA) is contacted with NaIO4 to produce the aldehyde derivative (Synthesis 1) depicted in FIG. 1. FIG. 2 presents analytical data for the HA-aldehyde.

Example 2: Synthesis of HA-Peptide Hydrazide

Figure 3:
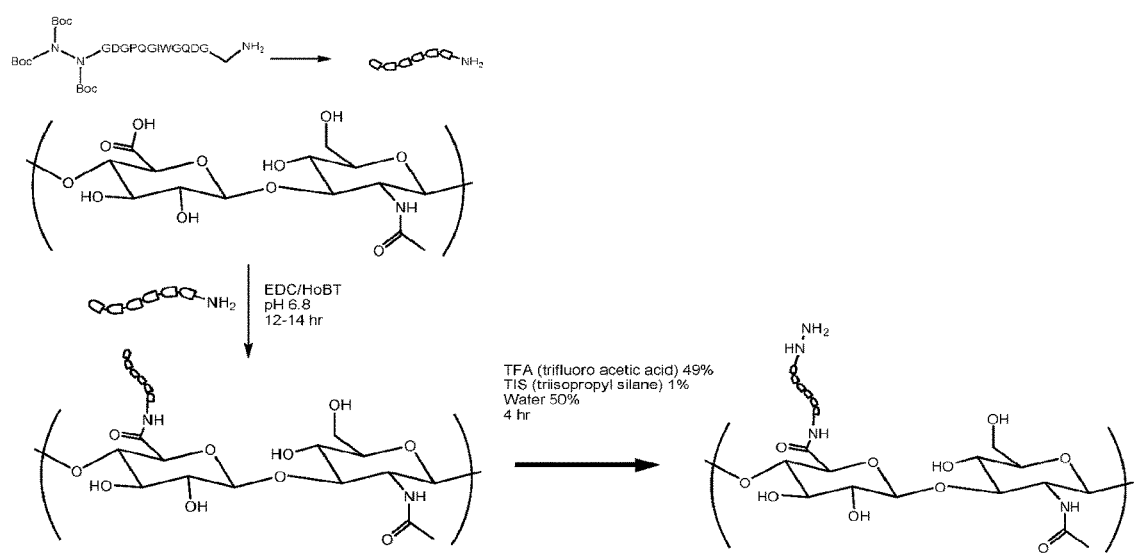
FIG. 3 illustrates synthesis of HA-peptide hydrazide for use in forming the hydrogel. The product has a hyaluronic acid backbone modified with either an aldehyde or a peptide with a hydrazide end.

Hyaluronic acid (HA) is contacted with EDC/HoBT at ph 6.8 for 12-14 hours to produce the intermediate depicted in FIG. 3. The intermediate is then contacted with trifluoroacetic acid (TFA, 49%), trisopropyl silane (TIS, 1%), and water (50%) for 4 hours to produce the hydrazide depicted in FIG. 3. EDC is ethyl-(N',N'-dimethylamino) propylcarbodiimide hydrochloride (EDC). HoBT is 1-hydroxybenzotriazole. One peptide that could be used is GCRDGPQGI-WGQDRCG (Seq. ID No. 5), which cleaves in the presence of MMP-2, but somewhat nonspecifically. In the example, the cross-linker utilized was of the formula (SEQ ID NOS 8 and 8 disclosed, respectively, in order of appearance):

the peptide being of the sequence GDGPQGIWGQDG.

Example 3: HA-Hydrazide Synthesis

Figure 4:
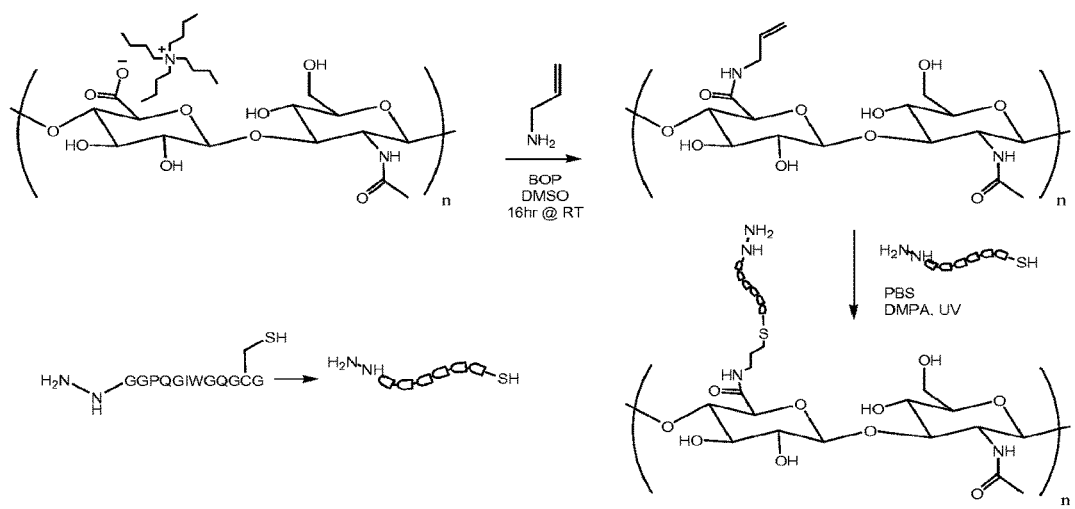
FIG. 4 illustrates synthesis of HA-hydrazide (Synthesis 2). The example depicted in the figure has 33% modification.
Figure 4:
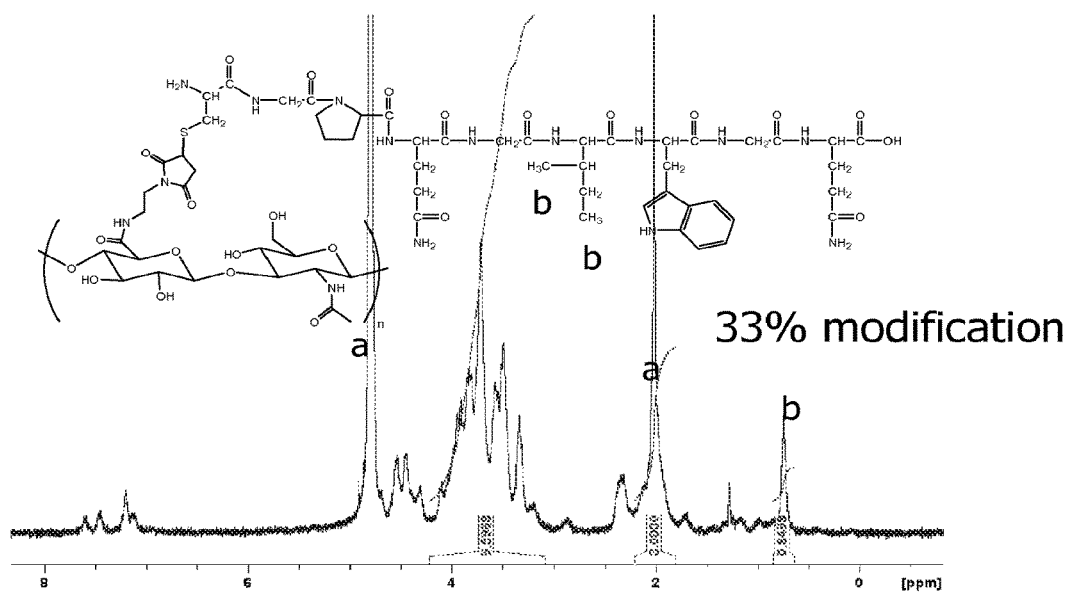

HA-hydrazide synthesis (Synthesis 2) having 33% modification was performed as depicted in FIG. 4. The peptide utilized was of the formula (Seq ID No. 6):

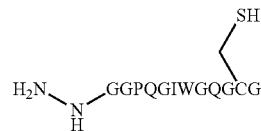

which is represented by the shorthand

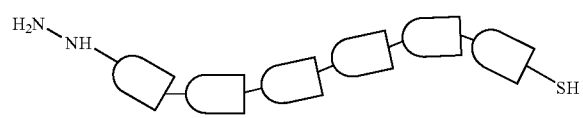

Analytical analysis of the product is also presented in FIG. 4.

Example 4: Hydrogel Formation

Figure 5:
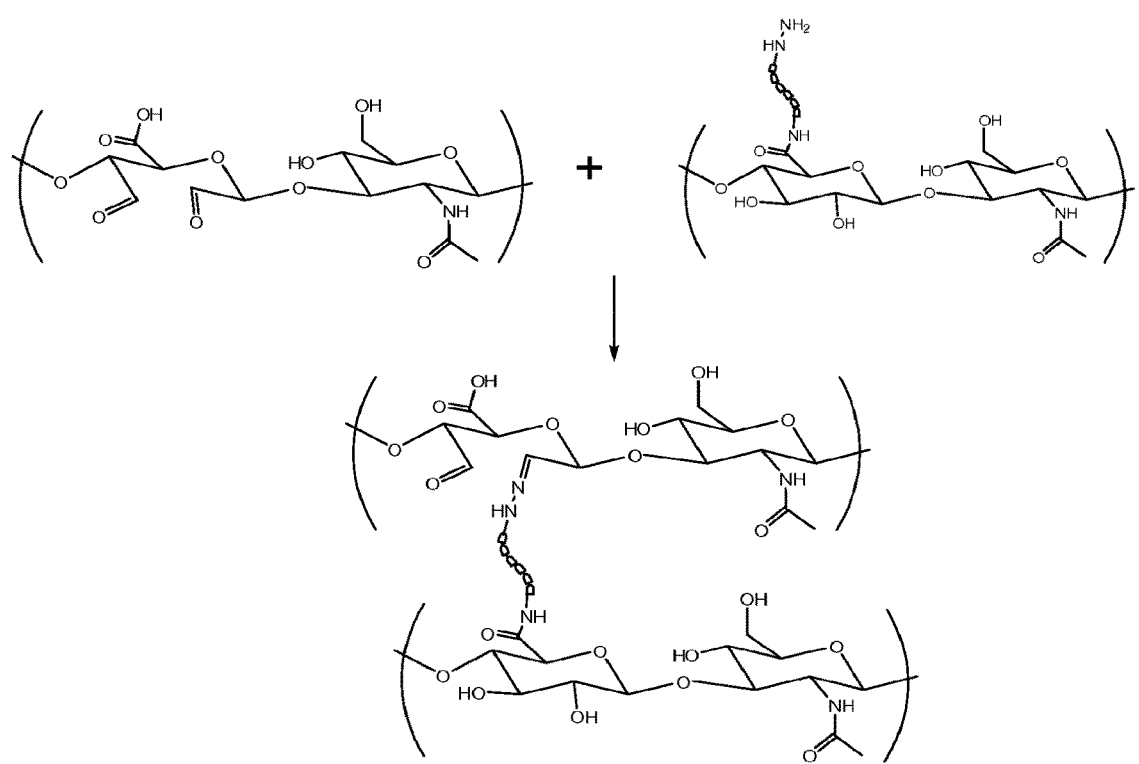
FIG. 5 illustrates formation of a hydrogel by mixing precursors containing a hyaluronic acid backbone modified with either an aldehyde or a peptide with a hydrazide end. By using a peptide that is MMP sensitive, the gel will form an enzyme sensitive hydrogel.

Hydrogel formed by mixing the aldehyde of Example 1 with the hydrazide of Example 2 to form the hydrogel depicted in FIG. 5.

Example 5: Gel Formation Through Mixing of Synthesis 1 and Synthesis 2

Figure 6:
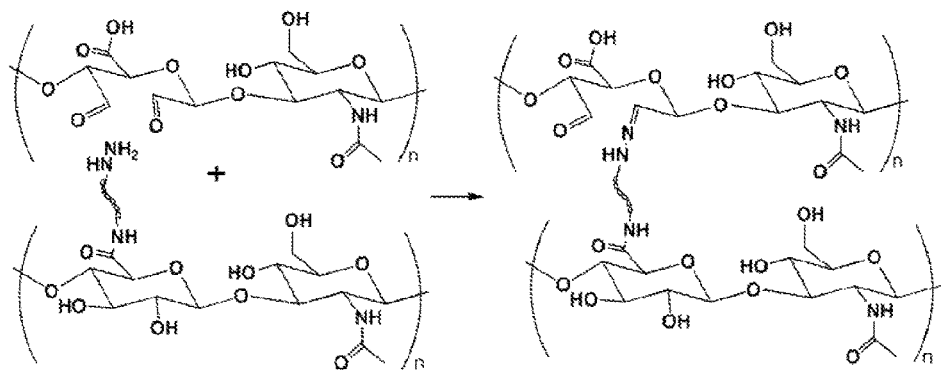
FIG. 6 illustrates gel formation through mixing of Synthesis 1 and Synthesis 2: hydrazone formation via hydrazide-aldehyde reaction. Gelation/properties can be controlled by HA modification and ratio of HA-aldehyde to HA-hydrazide.
Figure 6:
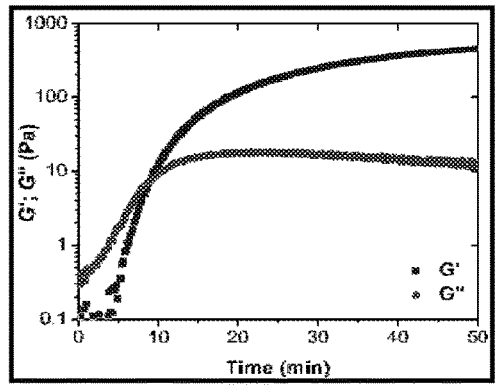
Figure 6:
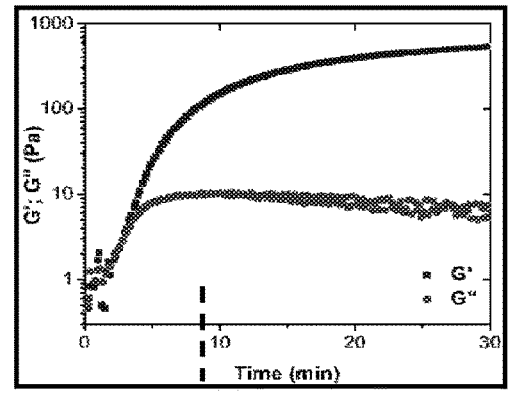

Gel was formed through a mixing of the products of synthesis 1 and synthesis 2 as presented in FIG. 6. Gelation/properties can be controlled by HA modification and ratio of HA-aldehyde to HA-hydrazide. Differences in time are illustrated by the plots presented in FIG. 6.

Example 6: MMP-Specific Gel Synthesis

Figure 7:
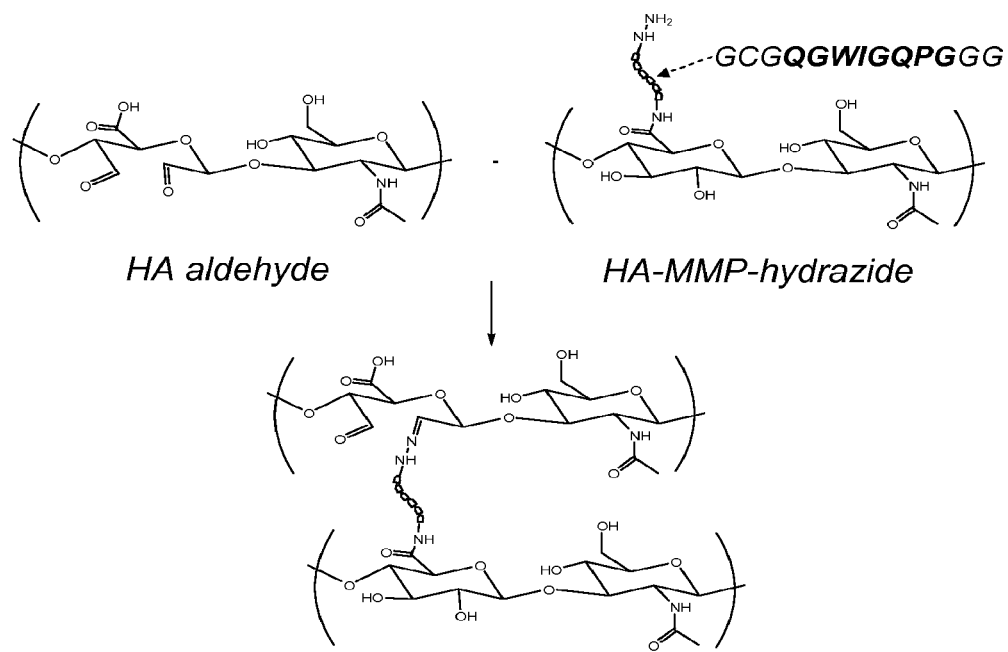
FIG. 7 illustrates a MMP-specific gel with a peptide crosslinker that responds to MMP-1, MMP-2.
Figure 8:
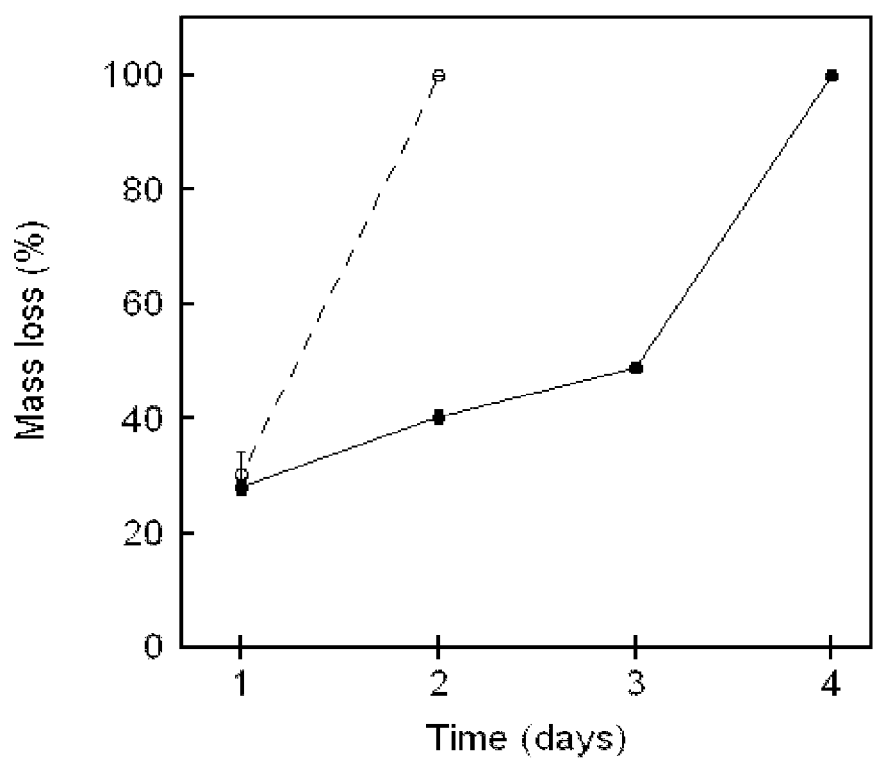
FIG. 8 illustrates mass loss with the gel of FIG. 7 as a function of time upon exposure to MMP (at day 1 or day 3).

FIG. 7 shows a MMP-specific gel with a peptide cross-linker that responds to MMP-1, MMP-2. In this example, the peptide has the sequence GCGQGWIGQPGGG (Seq. ID No. 7). Response to MMP of this gel is illustrated in FIG. 8.

Example 7: Crosslinking of an Acrylated Hyaluronic Acid

Figure 9:
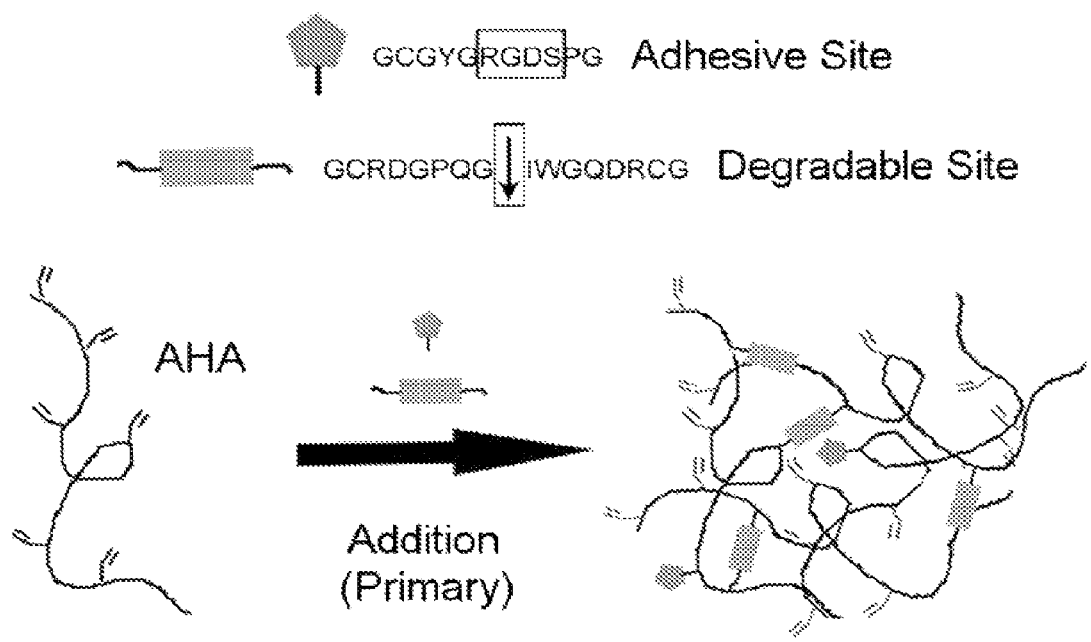
FIG. 9 illustrates the crosslinking of an acrylated hyaluronic acid with a peptide (containing thiols on each end).

Schematic of the crosslinking of an acrylated hyaluronic acid with a peptide (containing thiols on each end) if depicted in FIG. 9.

Example 8: Triggered Release of Ilomastat

Ilomastat was purchased from Sigma Aldrich. Ilomastat is also known as galardin or GM6001 and is of the following formula.

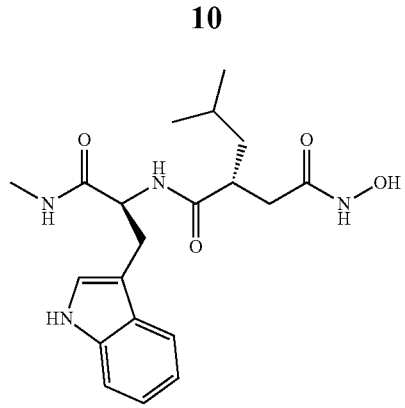

Ilomastat was ground into a fine powder of uniform microparticles. These microparticles were suspended in the dissolved HA-aldehyde and HA-hydrazide solutions at 10 µg per 100 µl, of polymer solution. At this concentration ilomastat remains a solid particle within the polymer solution. HA-aldehyde and HA-hydrazide polymers were mixed 1:1 aldehdye:hydrazide to induce crosslinking into a solid gel. The gels were incubated in phosphate buffered saline at 37° C. After 14 days less than 10% of the ilomastat was released from the gels due to hydrophobic interactions of the ilomastat in the microparticles. The gels were then exposed to collagenase 200 U/mL and the gels degraded. Once the gels were degraded, ilomastat was then solubilized in the larger volume of the buffer as evidenced by HPLC.

Example 9: Crosslinking of an Acrylated Hyaluronic Acid

Compositions described herein are administered to a patient for treatment of myocardial infarction, osteoarthritis, meniscal repair, ligament repair, or aortic aneurisms.

What is claimed:

1. A composition comprising:
   biocompatible hydrogel, comprising a plurality of cross-linkers connecting backbone components of said hydrogel; wherein said hydrogel is cross-linked utilizing a cross-linker comprising a peptide sequence that is capable of being degraded by a matrix metalloproteinase; said inhibitor being effective as a treatment of a condition related to the presence of said matrix metalloproteinase; wherein said hydrogel encapsulates and retains the inhibitor within the intact hydrogel through non-covalent interactions; wherein said hydrogel comprises one or more of hyaluronic acid, sulfated hyaluronic acid, sulfonated hyaluronic acid, dextran, dextran sulfate, sulfonated dextran, chondroitin sulfate, heparin and heparan sulfate; and
   a therapeutic agent comprising an inhibitor of matrix metalloproteinase.

2. The composition of claim 1, wherein said peptide sequence is incorporated into the cross-linker via reaction of thiol groups of cysteines with acrylates, methacrylates or maleimide groups.

3. The composition of claim 1, where said inhibitor of matrix metalloproteinase is TIMP-3.

4. The composition of claim 1, where said inhibitor of matrix metalloproteinase is a hydroxymate based compound such as ilomastat.

5. The composition of claim 1, where said inhibitor of matrix metalloproteinase is a tetracycline based compound such as doxycycline or a modified doxycycline.

6. The composition of claim 1, wherein said matrix metalloproteinase is MMP-13 or MMP-2.

7. The composition of claim 1, wherein said matrix metalloproteinase is MMP-1, MMP-8, or MM P-9.

8. The composition of claim 1, wherein said cross-linker comprises said peptide sequence and at least one of hyaluronic acid or polysaccharides.

9. The composition of claim 1, wherein said hydrogels comprise at least one of hyaluronic acid or other polysaccharide.

10. The composition of claim 1, wherein the composition is such that encapsulated inhibitors are released from the hydrogel and into the extracellular matrix of tissue in the presence of pathological levels of matrix metalloproteinase.

11. The composition of claim 1, wherein said peptide comprises a sequence GPQGIAGQ (SEQ ID NO: 4), GPQGIWGQ (SEQ ID NO: 3), GCRDGPQGIWGQDRCG (SEQ ID NO: 5), GGPQGIWGQGCG (SEQ ID NO: 6), or GCGQGWIGQPGGG (SEQ ID NO: 7).

12. The composition of claim 1, wherein the inhibitor of matrix metalloproteinase is useful in the treatment of myocardial infarction, osteoarthritis, meniscal repair, ligament repair, or aortic aneurisms.

13. The composition of claim 1, wherein inhibitor of matrix metalloproteinase reduces left ventricular remodeling associated with myocardial infarction in a patient.

14. The composition of claim 1, wherein said non-covalent interactions attenuate diffusion of encapsulated inhibitors from the hydrogel.

15. The composition of claim 1, wherein said non-covalent interactions are hydrophobic or electrostatic forces.

16. A process for treating myocardial infarction comprising administering to a patient in need of such treatment a composition of claim 1.

17. A process for treating osteoarthritis, meniscal repair, ligament repair or treating aortic aneurisms comprising administering to a patient in need of such treatment a composition of claim 1.

18. The process of claim 17, wherein said patient is a mammal.

19. The process of claim 17, wherein said patient is a human.

20. The process of claim 17, wherein said peptide sequence is incorporated into the cross-linker via reaction of thiol groups of cysteins with acrylates or methacrylates.

21. The process of claim 17, wherein said hydrogels comprise at least one of hyaluronic acid and polysaccharides.

22. A process for delivery of an inhibitor of matrix metalloproteinase comprising:
    administering a hydrogel of claim 1 to a patient;
    allowing said hydrogel to contact matrix metalloproteinase;
    said contact resulting in the release of at least a portion of said inhibitor of matrix metalloproteinase.

23. The process of claim 22, wherein said tissue inhibitor of matrix metalloproteinase is TIMP-3.

24. The process of claim 22, where said inhibitor of matrix metalloproteinase is ilomastat.

25. The process of claim 22, where said inhibitor of matrix metalloproteinase is doxycycline.

26. The process of claim 22, wherein said matrix metalloproteinase is MMP-13, MMP-2, MMP-8, MMP-9.

27. The process of claim 22, wherein the delivery is accomplished through a syringe or catheter.

* * * * *